(12) United States Patent
Fischell

(10) Patent No.: US 6,783,522 B2
(45) Date of Patent: Aug. 31, 2004

(54) IMPLANTABLE CATHETER HAVING AN IMPROVED CHECK VALVE

(75) Inventor: Robert E. Fischell, Dayton, MD (US)

(73) Assignee: Angel Medical Systems, Inc., Tinton Falls, NJ (US)

( * ) Notice: Subject to any disclaimer, the term of this patent is extended or adjusted under 35 U.S.C. 154(b) by 16 days.

(21) Appl. No.: 10/236,186

(22) Filed: Sep. 9, 2002

(65) Prior Publication Data

US 2004/0049169 A1 Mar. 11, 2004

(51) Int. Cl.[7] .................. A61M 25/16; A61M 25/18; A61M 5/00; A61M 31/00; A61M 37/00
(52) U.S. Cl. ................ 604/537; 604/246; 604/288.03
(58) Field of Search ............... 604/48, 93.01, 604/96.01, 98.01, 99.01, 99.02, 99.03, 99.04, 103.01, 264, 523, 524, 288.01, 288.02, 288.03, 288.04, 246, 247, 537

(56) References Cited

U.S. PATENT DOCUMENTS

| | | | | |
|---|---|---|---|---|
| 4,784,646 A | * | 11/1988 | Feingold | 604/175 |
| 4,846,810 A | * | 7/1989 | Gerber | 604/247 |
| 4,973,319 A | * | 11/1990 | Melsky | 604/247 |
| 5,030,210 A | * | 7/1991 | Alchas | 604/247 |
| 5,261,885 A | * | 11/1993 | Lui | 604/247 |
| 5,263,930 A | * | 11/1993 | Ensminger | 604/288.03 |
| 5,290,263 A | * | 3/1994 | Wigness et al. | 604/247 |
| 5,707,357 A | * | 1/1998 | Mikhail et al. | 604/167.03 |
| 5,707,361 A | * | 1/1998 | Slettenmark | 604/131 |
| 5,807,349 A | * | 9/1998 | Person et al. | 604/247 |

* cited by examiner

Primary Examiner—Brian L. Casler
Assistant Examiner—Mark K. Han

(57) ABSTRACT

Disclosed is a check valve for placement near the distal end of a catheter. A continuously smooth outer surface for the catheter with check valve system assures that there is no propensity for a blood clot to form in cracks on the system's outer surface. The check valve is a formed from a low durometer, highly elastic, elastomer cylindrical tube that is shrunk into a cylindrical groove that would typically be located near the catheter's distal end. When pressurized fluid is injected through the catheter, the cylinder that is placed over one or more holes in the cylindrical groove in the catheter is forced to expand radially outward which allows the fluid to be injected into the blood vessel. When the pressure is removed, the elastomer tube retracts to its normal position which position tightly covers the holes thereby preventing any blood from entering the catheter.

20 Claims, 2 Drawing Sheets

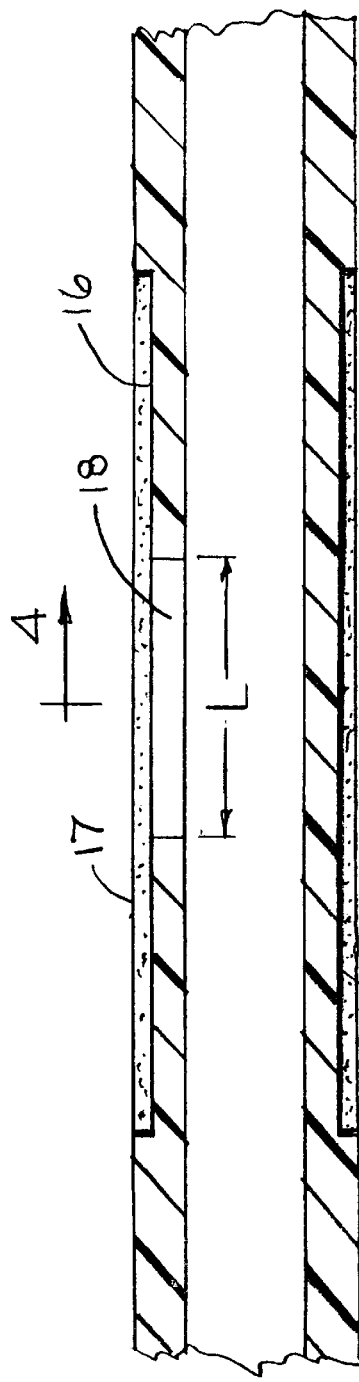
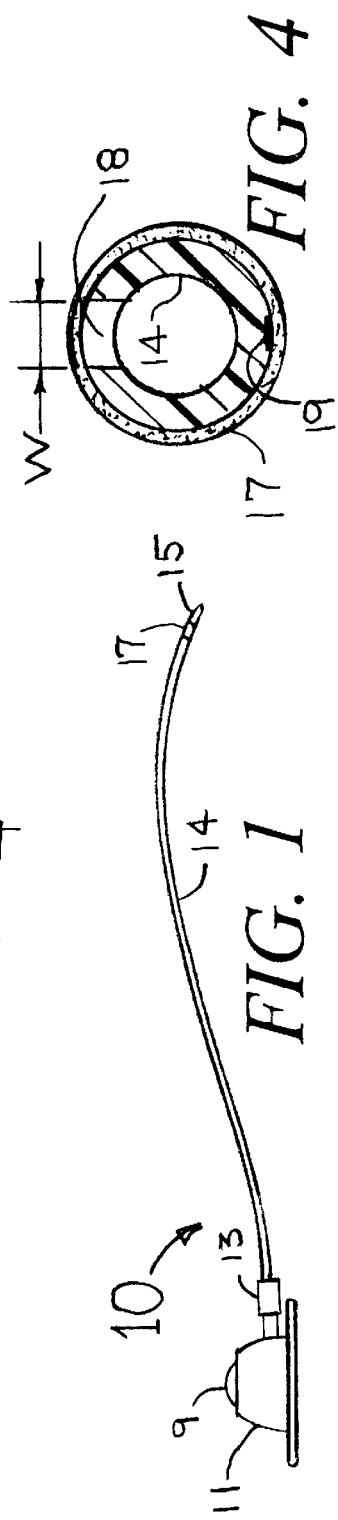

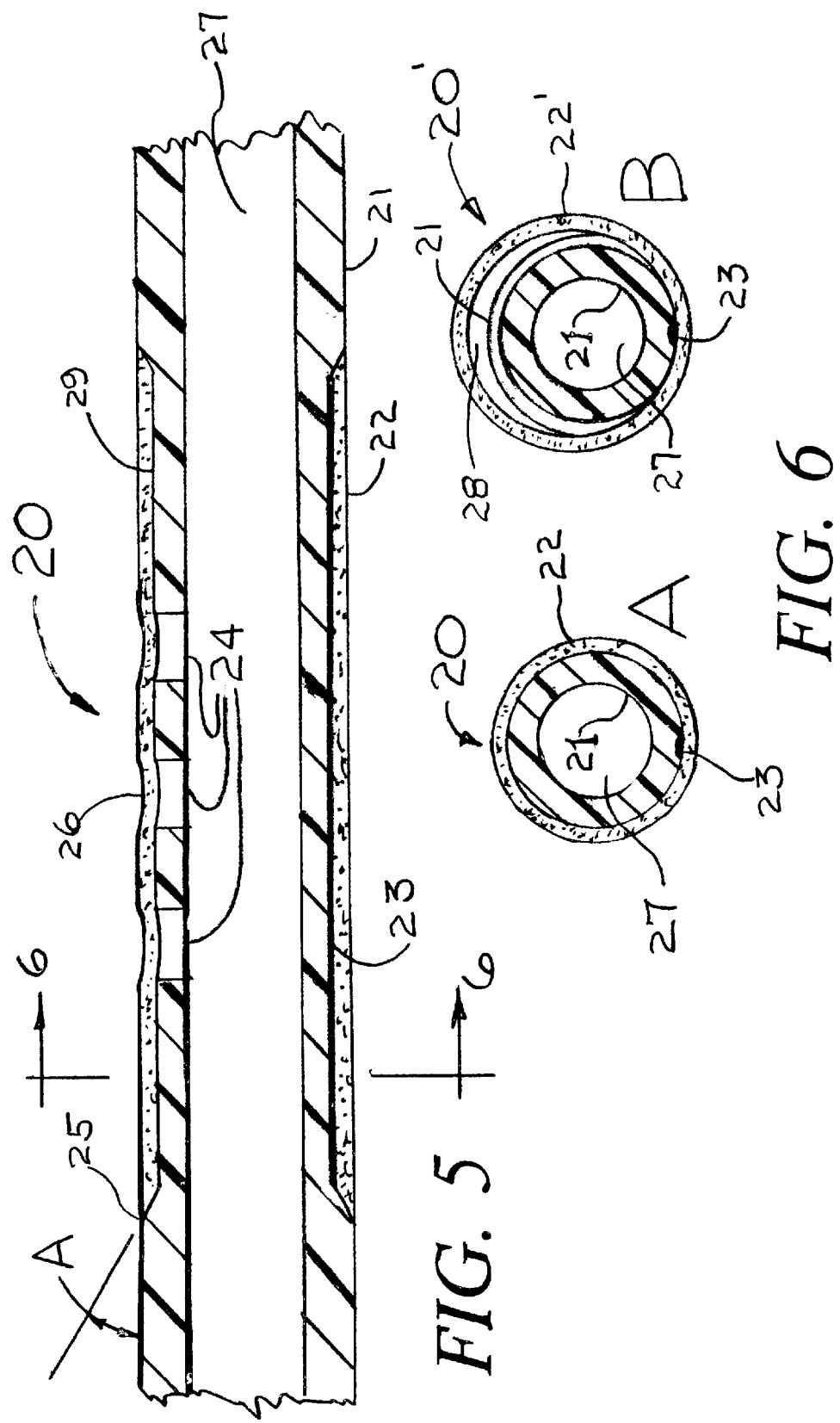

IMPLANTABLE CATHETER HAVING AN IMPROVED CHECK VALVE

FIELD OF USE

This invention is in the field of implantable medical devices that are used to inject medication into the vascular system of a human subject.

BACKGROUND OF THE INVENTION

There are many catheters that are used to deliver drugs into the vascular system of human subjects. Most of these catheters are open-ended which allows blood to flow into the catheter when no drug is being delivered. Although this is quite acceptable for short-term use, for catheters that remain implanted in a human subject for a time period between weeks and years, any open-ended catheter requires frequent flushing with saline solution or heparin to retain catheter patency. Although some catheters having a slit valve at their distal end to reduce this problem, there is still some opening possible between the sides of the slit where some blood can enter the catheter over long periods of time which can result in catheter blockage.

In U.S. Pat. No. 4,657,536, F. D. Dorman describes a check valve that can be used at the end of an indwelling catheter. However, Dorman's check valve does not have a flexible tip to minimize damage to the arterial wall during placement and for preventing damage to the wall of a blood vessel if the catheter remains implanted for several years. Furthermore, the Dorman check valve does not have a continuously smooth outer surface which lack of smoothness can cause some accumulation of blood clots that could interfere with the operation of the valve. Still further, Dorman does not teach the use of a catheter check valve in conjunction with an implantable drug port where the use of an improved, long-lived check valve would be particularly valuable.

SUMMARY OF THE INVENTION

The present invention is a check valve for placement near the distal end of a catheter. This check valve has an extraordinarily simple design so that it would operate in a highly reliable manner. The check valve design allows for a continuously smooth outer surface for the catheter with check valve system so that there is no propensity for a blood clot to form in cracks on the system's outer surface. The check valve is also designed specifically to disallow any part of the valve from separating from the catheter. This attribute prevents the creation of a foreign body that could pass downstream and cause blood flow to be stopped at some part of the vascular system.

The check valve is a formed from a low durometer, highly elastic, elastomer cylindrical tube that is shrunk into a cylindrical groove that would typically be located near the catheter's distal end. When pressurized fluid is injected through the catheter, the cylinder that is placed over one or more holes in the cylindrical groove in the catheter is forced to expand radially outward which allows the fluid to be injected into the blood vessel. When the pressure is removed, the elastomer tube retracts to its normal position which position tightly covers the holes thereby preventing any blood from entering the catheter.

The catheter can be designed to have a flexible tip and a generally hemispherical shape at its distal end so as to decrease the chance of any damage to a vessel wall during insertion or long term use of the catheter. Furthermore, the catheter with distal check valve system is ideally suited to be used with an implanted drug port for the long-term administration of drugs. Such drug administration may take place over a period of years. To retain patency for such a long-term indwelling catheter, present practice is to use a slit-valve at the end of the catheter and/or to frequently flush an open-ended catheter with heparin or at least with a saline solution. An important advantage of the present invention is that a catheter with such a check valve could retain its patency within the vascular system of a human subject for many years without ever requiring flushing of any sort and without even having a crack in the catheter's wall. Not requiring frequent flushing would save on the time and expense of medical personnel and would be less painful for the patients. The present invention, when in the form of a pass-through drug port, is ideally suited to be used in conjunction with an implanted cardiosaver system as described in U.S. patent application Ser. No. 10/051,743 by R. E. Fischell, et al.

Thus an object of this invention is to have a catheter that is placed for weeks to years within a blood vessel of a human subject, which catheter has a check valve with a continuously smooth outer surface to preclude any blood clot from forming on that outer surface.

Another object of the invention is to have a generally hemispherical distal end of the catheter that is also of a soft plastic so as to reduce the possibility of damage to the vessel wall during insertion and long-term usage.

Still another object of this invention is to form the check valve from a single cylindrical tube of a low durometer, highly elastic elastomer that is fixedly attached within a cylindrical groove near the catheter's distal end, which groove provides further assurance that the cylindrical tube will not inadvertently become separated from the catheter.

Still another object of this invention is to shape the distal and proximal ends of the cylindrical tube check valve to be angled with respect to the longitudinal axis of the catheter to create a connection between the cylindrical tube and the catheter that provides for a continuously smooth outer surface where the cylindrical tube joins the catheter.

Still another object of this invention is to have the catheter filled with a solution after completion of a drug injection, which solution has essentially the same osmolality as blood so as to prevent any salts or liquid within the blood from passing by osmosis through the wall of the catheter into the catheter's lumen.

Still another object of this invention is to have the catheter filled with a solution after completion of a drug injection, which solution includes an anti-bacterial agent to prevent bacteria from growing within the catheter.

Still another object of this invention is to use the check-valved catheter system with an implanted drug port for the long-term administration of fluids into a human subject.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1 illustrates an implantable drug port with attached catheter having a check valve located near the catheter's distal end.

FIG. 2 is a longitudinal cross section of a distal portion of the catheter with a check valve.

FIG. 3 is an enlarged longitudinal cross section showing details of the check valve.

FIG. 4 is the transverse cross section of the check valve at section 4—4 of FIG. 3.

FIG. 5 is a longitudinal cross section of an alternative embodiment of the check valve which has an angled joint at the proximal and distal ends of the cylindrical tube which is the check valve.

FIG. 6A is the transverse cross section of the check valve at section 6—6 of FIG. 5 showing the check valve in its normal, closed position.

FIG. 6B is a transverse cross section of the check valve in its open position for delivering a drug into a blood vessel of a human subject.

DETAILED DESCRIPTION OF THE INVENTION

FIG. 1 illustrates an implantable drug port system 10 that includes a main body 11 which has a self-sealing septum 9. The main body 11 has a connector 13 to which a catheter 14 is attached. An example of a similar port is Product No. AP 06016 as marketed by Arrow International, Inc. The distal end of the catheter 14 has a generally hemispherical shape to minimize damage to the vessel walls where the catheter is inserted into a blood vessel of a human subject. Near the distal end of the catheter is a cylindrical tube 17 that is the check valve of the present invention.

FIG. 2 is a longitudinal cross section of a distal portion of the catheter 14 having an elastomer cylindrical tube check valve 17 that is placed over an opening 18. FIG. 2 also shows a generally hemispherical, smooth distal tip of the catheter. The end portion 15 of the catheter can be formulated from a softer (lower durometer) plastic as compared to the catheter 14. This attribute results in minimizing trauma to the vessel wall during insertion and long-term use. The tip 15 is joined to the main cylindrical portion of the catheter 14 at the junction 15A.

FIG. 3 is an enlarged longitudinal cross section of the portion of the catheter 14 where the cylindrical tube check valve 17 is placed over a cylindrical groove 16 of essentially the same length as the tube 17, which groove 16 is formed into the catheter 14. An opening 18 having a length "L" is placed in the groove 16 directly under the check valve 17. The length "L" of the groove 16 is typically between 5% and 95% as long as the length of the cylindrical tube check valve 17. The length of the tube 17 should be approximately between 1 and 10 mm. An adhesive strip 19 on the side of the groove 16 opposite the opening 18 is used to fixedly attach the tube 17 into the groove 16 of the catheter 14. The attachment of the tube 17 to the catheter 14 could also be accomplished by ultrasonic welding of the tube 17 to the catheter 14. It is clearly seen from FIG. 3 that, even if the tube 17 is not joined to the catheter 14 by means of an adhesive or by ultrasonic welding, the edges of the cylindrical groove 16 would by themselves cause the tube 17 to remain in the position shown in FIG. 3. To further guarantee that the tube 17 will not come out of the groove in the catheter 14, the tube 17 would be shrunk into the cylindrical groove 16. As is well known in the art of catheters, shrinking the tube 17 into the groove 16 can be accomplished by solvent swelling of the tube 17, placing it over the groove and then allowing the solvent to evaporate which causes the tube 17 to shrink into the groove 16. This effect can also be accomplished by heat shrinking of the tube 17. In either case, the final inside diameter of the shrunk tube 17, if unrestrained by the cylindrical groove 16, would be smaller than the outer diameter of the groove 16. This causes the tube 17 to be in tension which provides further assurance of a tight seal over the opening 18. The hoop tension of the tube 17 also further guarantees that it will not come off the catheter 14 when fluid is injected into the catheter 14.

FIG. 4 is a transverse cross section of the catheter 14 at section 4—4 of FIG. 3 showing the catheter 14, tube 17, opening 18 and adhesive strip 19. The opening 18 should have a width "W" that is approximately between 10% and 95% of the inside diameter of the catheter 14.

FIG. 5 is a preferred embodiment of a distal portion of a check valve and catheter system 20 which includes a catheter 21 having a central lumen 27 and a generally cylindrical groove 29. A multiplicity of holes 24 are placed through the wall of the catheter 21 within the generally cylindrical groove 29. Ideally there would be between one and ten of such holes, each of which could have a diameter that lies approximately between 10% and 95% of the inside diameter of the catheter 21. The holes 24 can have a variety of distributions within the groove 29, but an optimum distribution would have approximately three holes 24 aligned in an axial direction. The inside diameter of the catheter 21 would typically be between 0.2 and 5 mm, and the length of the groove 29 would typically be between 0.5 and 10 mm. Shrunk into the groove 29 is a generally cylindrical elastomer tube check valve 22 that can be fixedly attached to the groove 29 by means of an adhesive strip 23 (or ultrasonic bond) along a line that is diametrically opposite from the holes 24. Because the tube 22, if unrestrained by the groove 29, would have an inside diameter that is smaller than the outside diameter of the groove 29, there is formed an indentation 26 of the tube 22 into the holes 24. Such indentations still provide a continuously smooth, crack-free outer surface for the check valve catheter system 20 so that there will be no tendency for blood clots to form on the system's outer surface.

An important aspect of the design of the system 20 is the angled junction 25 where the proximal and distal ends of the tube 22 join to the proximal and distal ends of the groove 29. The angled junction 25, when used with a tube 22 that is shrunk into the groove 29, assures that there will be no crack formed at the junction 25 into which a blood clot could form. If formed, such a blood clot could prevent the proper functioning of the check valve. The optimum angle "A" for the angled junction 25 would be approximately between 10 and 60 degrees with respect to the longitudinal axis of the catheter 21.

FIGS. 6A and 6B are transverse cross sections of the system 20 at section 6—6 of FIG. 5. FIG. 6A shows the normal, unactuated position of the tube 22 and FIG. 6B shows the position of the tube 22' when pressurized fluid is being delivered through the lumen 27 of the catheter 21. FIG. 6A shows the catheter 21 having a lumen 27 and the tube 22 fixedly attached to the catheter 21 by an adhesive strip 23. In the position of the tube 22 shown in FIGS. 5 and 6A, no blood from the vascular system of the human subject can enter into the lumen 27. When a drug under pressure is placed through the lumen 27, the open system 20' is formed as shown in FIG. 6B. The pressurized drug would force an opening 28 to form between the catheter 21 and the expanded tube 22'. Thus the drug can be delivered into the vascular system of the human subject. After the injection of drug is completed, the expanded tube 22' will return to its normal diameter as shown for the tube 22 of FIGS. 5 and 6A.

FIGS. 1–3 and 5 clearly show an elongated cylindrical catheter 14 or 21 and check valves 17 and 22 which together have a continuously smooth outer surface that would preclude the formation of blood clots on the systems outer surface, which blood clots could interfere with the functioning of the check valves. This superior design should provide highly reliable performance within a human artery or vein for many years without requiring frequent flushing with saline or heparin. Although the catheter with check valve described herein is well suited for use with an implanted drug port, it should be understood that the catheter plus check valve can be used with any percutaneous drug delivery systems as well as any form of implanted drug delivery system.

Although catheters formed from a single plastic material are shown in FIGS. 2–5, it should be understood that the catheters could be formed with one plastic material on the inside of the catheter and a second plastic material coaxially extruded over the first material. Plastic materials such as (but not limited to) polyurethane, polyethylene, silicon rubber, Teflon and Nylon can be used to form the catheter or for either layer of a two layer catheter. Furthermore, any plastic material that is a low durometer, highly elastic, biocompatible elastomer can be used for the check valve. Examples of such a plastic are (but are not limited to) polyurethane, polyethylene and silicone rubber.

It is expected that this simple check valve, which is merely a single elastomer tube placed over one or more openings, would be simple to build and operate and therefore it would be comparatively inexpensive and highly reliable. Furthermore, it is expected that the designs described herein would have distinct advantages over slit-valve catheters which have a crack that can have a blood clot formed therein and also those catheters typically require some periodic flushing at least with saline solution. Still further, the present invention can clearly be used in conjunction with multi-lumen catheters such as central venous catheters. In this regard, one or more lumens could have a check valve and one or more other lumens could have a continuous fluid connection into the blood vessel or have a slit valve. Furthermore, although FIGS. 1 and 2 show the check valve to be located near the catheter's distal end, it should be understood that the check valve is able to be located anywhere along the length of the catheter.

When not injecting a drug or any other type of liquid through the catheter, it is desirable to retain a solution in the catheter that has the same osmolality as blood. This attribute would diminish any tendency for changing the nature of the liquid within the catheter because of osmosis of some component of the blood through the catheter wall. For this purpose, a normal saline solution could be used. The solution could also contain some anti-bacterial agent to prevent bacteria from forming within the catheter.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A system for injecting a liquid into a blood vessel of a human subject, the system including an elongated tube catheter and a check valve formed from a generally cylindrical, elastomer tube that is placed into a groove formed into the wall of the catheter near the catheter's distal end, the outer surface of the check valve and catheter forming together a continuously smooth outer surface, the catheter also having at least one opening through the catheter's wall and within the groove through which opening pressurized liquid can cause the check valve to open thereby allowing the liquid to be injected into the blood of the human subject.

2. The system of claim 1 wherein the catheter has a generally hemispherical distal end thereby decreasing the possibility of trauma to the blood vessel wall during insertion of the system into the human subject.

3. The system of claim 1 wherein a distal portion of the catheter is formed from an elastomer having a lower durometer as compared to the durometer of the plastic from which the catheter is formed.

4. The system of claim 1 wherein the elastomer tube check valve is shrunk into the groove in the catheter.

5. The system of claim 1 wherein the catheter is attached at its proximal end to the main body of an implanted drug port.

6. The system of claim 1 wherein the elastomer tube check valve is fixedly attached to the outer surface of the groove in the catheter by either an adhesive bond or by ultrasonic welding.

7. The system of claim 6 wherein the adhesive bond or ultrasonic weld is located at a position that is generally diametrically opposite the location of the at least one opening in the wall of the catheter.

8. The system of claim 1 wherein the catheter is formed from a plastic material selected from the group consisting of polyurethane, polyethylene, silicone rubber, Nylon, Teflon or a combination of one or more of such plastic materials.

9. The system of claim 1 wherein the cylindrical tube check valve is fabricated from a highly elastic, biocompatible, elastomer selected from the group consisting of polyurethane, polyethylene, silicone rubber or any comparable highly elastic material.

10. The system of claim 1 wherein the proximal and distal ends of the check valve form an angled junction with angled proximal and distal ends of the groove, the angle of the angled junction being between 10 and 60 degrees relative to the longitudinal axis of the catheter.

11. A subcutaneously implanted drug port for the long-term administration of a liquid into a human subject, the drug port including an elastomer septum placed just below the skin of the human subject, the septum being part of the main body of the drug port to which is attached the proximal end of a catheter that has a check valve located near the catheter's distal end, the check valve being formed from a cylindrical tube of a highly elastic elastomer that is placed within a groove located in the catheter near its distal end and the catheter also having at least one hole through the catheter's wall and within the groove in the catheter, the check valve and the catheter forming together a continuously smooth outer surface to preclude the formation of blood clots on the outer surface of the catheter and check valve.

12. The system of claim 11 wherein the catheter has a generally hemispherical distal end thereby decreasing the possibility of trauma to the blood vessel wall during insertion of the system into the human subject.

13. The system of claim 11 wherein a distal portion of the catheter is formed from an elastomer having a lower durometer as compared to the durometer of the plastic from which the catheter is formed.

14. The system of claim 11 wherein the elastomer tube check valve is shrunk into the groove in the catheter.

15. The system of claim 11 wherein the elastomer tube check valve is fixedly attached to the outer surface of the groove in the catheter by either an adhesive bond or by ultrasonic welding.

16. The system of claim 15 wherein the adhesive bond or ultrasonic weld is located at a position that is generally diametrically opposite the location of the at least one opening in the wall of the catheter.

17. The system of claim 11 wherein the catheter is formed from a plastic material selected from the group consisting of polyurethane, polyethylene, silicone rubber, Nylon, Teflon or a combination of one or more of such plastic materials.

18. The system of claim 11 wherein the cylindrical tube check valve is fabricated from a highly elastic elastomer selected from the group consisting of polyurethane, polyethylene, silicone rubber or any comparable highly elastic material.

19. The system of claim 11 wherein the catheter has its lumen filled with a liquid that has approximately the same osmolality as human blood so as to prevent the passing by osmosis of any portion of the blood into the lumen of the catheter.

20. The system of claim 11 wherein the catheter has its lumen filled with a liquid that includes an anti-bacterial agent.

* * * * *